(12) United States Patent
Stadler et al.

(10) Patent No.: US 11,911,622 B2
(45) Date of Patent: Feb. 27, 2024

(54) CONDUCTION SYSTEM PACING WITH ADAPTIVE TIMING TO MAINTAIN AV AND INTERVENTRICULAR SYNCHRONY

(71) Applicant: Medtronic, Inc., Minneapolis, MN (US)

(72) Inventors: Robert W. Stadler, Shoreview, MN (US); Subham Ghosh, Blaine, MN (US); Jian Cao, Shoreview, MN (US); Andrea Grammatico, Rome (IT); Sarah Meloni, Rome (IT); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 234 days.

(21) Appl. No.: 17/468,058

(22) Filed: Sep. 7, 2021

(65) Prior Publication Data

US 2022/0088390 A1    Mar. 24, 2022

Related U.S. Application Data

(60) Provisional application No. 63/081,596, filed on Sep. 22, 2020.

(51) Int. Cl.
*A61N 1/368* (2006.01)
*A61B 5/366* (2021.01)
(Continued)

(52) U.S. Cl.
CPC ............ *A61N 1/3684* (2013.01); *A61B 5/353* (2021.01); *A61B 5/366* (2021.01); *A61N 1/37512* (2017.08)

(58) Field of Classification Search
CPC .... A61N 1/368; A61N 1/3682; A61N 1/3684; A61N 1/36843
See application file for complete search history.

(56) References Cited

U.S. PATENT DOCUMENTS 4,421,116 A    12/1983  Markowitz
5,312,445 A    5/1994   Nappholz et al.
(Continued)

FOREIGN PATENT DOCUMENTS

EP    0118306 A1    3/1984

OTHER PUBLICATIONS

Ali et al., "The Emerging Role of Cardiac Conduction System Pacing as a Treatment for Heart Failure," Current Heart Failure Reports, vol. 17, No. 5, https://doi.org/10.1007/s11897-020-00474-y, Aug. 28, 2020, pp. 288-298.
(Continued)

*Primary Examiner* — George R Evanisko
(74) *Attorney, Agent, or Firm* — Shumaker & Sieffert, P.A.

(57) ABSTRACT

An implantable medical device system is configured to generate signals representing activity of a heart of a patient; determine, based on the signals, an intrinsic delay of the heart of the patient; determine whether the intrinsic delay is indicative of a first-degree heart block being present in the heart of the patient; determine a patient-specific timing regime for conduction system pacing based on whether the intrinsic delay is indicative of the first-degree heart block being present in the heart of the patient; and administer cardiac pacing to a native conduction system of the heart of the patient based on the timing regime.

23 Claims, 5 Drawing Sheets

(51) Int. Cl.
*A61B 5/353* (2021.01)
*A61N 1/375* (2006.01)

(56) References Cited

U.S. PATENT DOCUMENTS

| | | | |
|---|---|---|---|
| 5,861,007 A | 1/1999 | Hess et al. | |
| 6,311,088 B1 | 10/2001 | Betzold et al. | |
| 6,622,040 B2 | 9/2003 | Ding et al. | |
| 6,804,555 B2 | 10/2004 | Warkentin | |
| 7,912,544 B1 | 3/2011 | Min et al. | |
| 7,941,217 B1 | 5/2011 | Pei et al. | |
| 8,483,825 B2 | 7/2013 | Yu et al. | |
| 8,954,138 B2 | 2/2015 | Maskara et al. | |
| 9,352,159 B2 | 5/2016 | Fishel | |
| 9,399,139 B2 | 7/2016 | Demmer et al. | |
| 9,687,654 B2 | 6/2017 | Sheldon et al. | |
| 9,713,432 B2 | 7/2017 | Patangay et al. | |
| 10,272,248 B2 | 4/2019 | Engels et al. | |
| 10,532,213 B2 | 1/2020 | Ghosh | |
| 2009/0234411 A1 | 9/2009 | Sambelashvili et al. | |
| 2009/0299423 A1 | 12/2009 | Min | |
| 2014/0172035 A1 | 6/2014 | Shuros et al. | |
| 2019/0009095 A1 | 1/2019 | Sheldon et al. | |
| 2019/0054297 A1 | 2/2019 | Zhang et al. | |
| 2019/0111264 A1 | 4/2019 | Zhou | |
| 2019/0111265 A1 | 4/2019 | Zhou | |
| 2020/0179705 A1* | 6/2020 | Ternes | A61N 1/3702 |

OTHER PUBLICATIONS

International Search Report and Written Opinion of International Application No. PCT/US2021/050199, dated Jan. 10, 2022, 10 pp.

"AdaptivCRT Feature," Medtronic, retrieved at https://www.medtronicacademy.com/features/adaptivcrt-feature, May 31, 2020, 4 pp.

Bohora, "AV Interval Optimization—A Step Towards Physiological Pacing in Patients with Normal Left Ventricular Function," Indian Pacing and Electrophysiology Journal, vol. 10, No. 9, Sep. 5, 2010, pp. 379-382.

Daoud et al., "Cardiac Resynchronization Therapy Pacemaker: Critical Appraisal of the Adaptive CRT-P Device," Medical Devices, vol. 9, Jan. 18, 2016, 13 pp.

* cited by examiner

CONDUCTION SYSTEM PACING WITH ADAPTIVE TIMING TO MAINTAIN AV AND INTERVENTRICULAR SYNCHRONY

This application claims the benefit of U.S. Provisional Patent Application 63/081,596, filed Sep. 22, 2020, the entire content of which is incorporated by reference.

TECHNICAL FIELD

The disclosure relates generally to medical device systems and, more particularly, cardiac therapy delivery by implantable medical devices.

BACKGROUND

Some types of implantable medical devices, such as cardiac pacemakers or implantable cardioverter defibrillators, provide electrical therapy to a heart of a patient via electrodes of one or more implantable leads. The electrical therapy may be delivered to the heart in the form of pulses or shocks for pacing, cardioversion or defibrillation. In some cases, an implantable medical device may sense intrinsic depolarizations of the heart and control the delivery of electrical therapy to the heart based on the sensing.

Cardiac resynchronization therapy (CRT) is one type of electrical therapy delivered by an implantable medical device. Cardiac resynchronization therapy may help enhance cardiac output by resynchronizing the electromechanical activity of the ventricles of the heart and between one or more atria of the heart and the ventricles of the heart. Ventricular dyssynchrony may occur in patients that suffer from congestive heart failure (CHF). Atrioventricular dyssynchrony may occur when contraction of one or more ventricles of the heart are not properly synchronized with contractions of one or more atria of the heart. Implantable medical device systems that deliver CRT often include three leads to respectively place electrodes in or near the right atrium, right ventricle, and left ventricle, for separate pacing and/or sensing in each of these chambers.

Conduction system pacing is a technology that uses the heart's native conduction system to provide paced depolarizations and resulting contractions that better mimic intrinsic depolarizations and contractions, which may improve the health and pumping efficiency of the heart. Example types of conduction system pacing include His bundle pacing, left bundle branch area pacing (LBBAP), right bundle branch area pacing (RBBAP), and ventricular pacing from the atrium (VfromA).

SUMMARY

In general, this disclosure is directed to techniques for controlling the delivery of conduction system pacing. Proper pace timing for conduction system pacing delivered by an implantable medical device system is important in order to achieve atrioventricular (AV) synchrony and interventricular synchrony. This disclosure describes techniques for automatically determining a patient-specific timing regime to achieve AV and/or interventricular synchrony.

Delivering conduction system pacing using a patient-specific timing regime according to the techniques of this disclosure may provide a degree of cardiac resynchronization that is comparable to traditional technologies for providing CRT. Conduction system pacing may have benefits over traditional technologies for providing CRT because conduction system pacing may be able to take advantage of synchronous depolarization from the heart's native conduction system and may utilize fewer leads and/or deliver pulses to fewer cardiac chambers per cardiac cycle. Use of the techniques described in this disclosure may increase the benefits of the implantable medical device system to the patient, conserve battery power of the implantable medical device system, and/or provide other benefits.

In one example, this disclosure describes a method comprising: generating, by sensing circuitry of an implantable medical device system, signals representing activity of a heart of a patient; determining, by processing circuitry of the implantable medical device system, based on the signals, an intrinsic delay of the heart of the patient; determining, by the processing circuitry, whether the intrinsic delay is indicative of a first-degree heart block being present in the heart of the patient; determining, by the processing circuitry, a patient-specific timing regime for conduction system pacing based on whether the intrinsic delay is indicative of the first-degree heart block being present in the heart of the patient; and administering, by therapy delivery circuitry of the implantable medical device system, cardiac pacing to a native conduction system of the heart of the patient based on the patient-specific timing regime.

In another example, this disclosure describes an implantable medical device system comprising: sensing circuitry configured to generate signals representing activity of a heart of a patient; processing circuitry configured to: determine, based on the signals, an intrinsic delay of the heart of the patient; determine whether the intrinsic delay is indicative of a first-degree heart block being present in the heart of the patient; and determine a patient-specific timing regime for conduction system pacing based on whether the intrinsic delay is indicative of the first-degree heart block being present in the heart of the patient; and therapy delivery circuitry configured to administer cardiac pacing to a native conduction system of the heart of the patient based on the patient-specific timing regime.

In another example, this disclosure describes a non-transitory computer-readable medium storing instructions for causing processing circuitry of an implantable medical device system to perform a method in accordance with one or more techniques of this disclosure.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

DETAILED DESCRIPTION

In general, this disclosure describes example techniques related to conduction system pacing. Conduction system pacing is a technique in which one or more pacemaker devices use the heart's native electrical conduction system to conduct electrical signals that cause depolarization of heart muscles, which ultimately causes synchronous contraction of the ventricles. Implantable medical device systems that perform conduction system pacing should generate electrical impulses based on a timing regime so that the patient's heart achieves atrioventricular (AV) synchrony and interventricular synchrony.

Achieving AV synchrony and interventricular synchrony may be challenging when using conduction system pacing because electrical signals associated with cardiac activation can travel through the heart at different rates in different patients. For example, if a patient has first-degree heart block, electrical signals may arrive in the His bundle, left bundle branch, or right bundle branch with a greater delay than in patients that do not have first-degree heart block. Moreover, different patients may have different amounts of interventricular dyssynchrony. Another factor that complicates the problem of achieving AV synchrony and interventricular synchrony is that levels of AV dyssynchrony and interventricular dyssynchrony may change depending on the patient's overall heart rate. For instance, if the patient's overall heart rate is above or below a particular level, the patient's heart may no longer exhibit AV dyssynchrony and/or interventricular dyssynchrony.

This disclosure describes implantable medical device systems that are configured to automatically determine a patient-specific timing regime and configured to apply conduction system pacing, e.g., for CRT, based on the patient-specific timing regime. For instance, in accordance with an example of this disclosure, sensing circuitry of an implantable medical device system, generates signals representing activity of a heart of a patient. Processing circuitry of the implantable medical device system determines, based on the signals, an intrinsic delay of the heart of the patient. Additionally, the processing circuitry determines whether the intrinsic delay is indicative of a first-degree heart block being present in the heart of the patient. The processing circuitry may further determine a patient-specific timing regime for conduction system pacing based on whether the intrinsic delay is indicative of the first-degree heart block being present in the heart of the patient. Therapy delivery circuitry of the implantable medical device system may deliver conduction system pacing, e.g., for CRT, based on the patient-specific timing regime.

Figure 1:
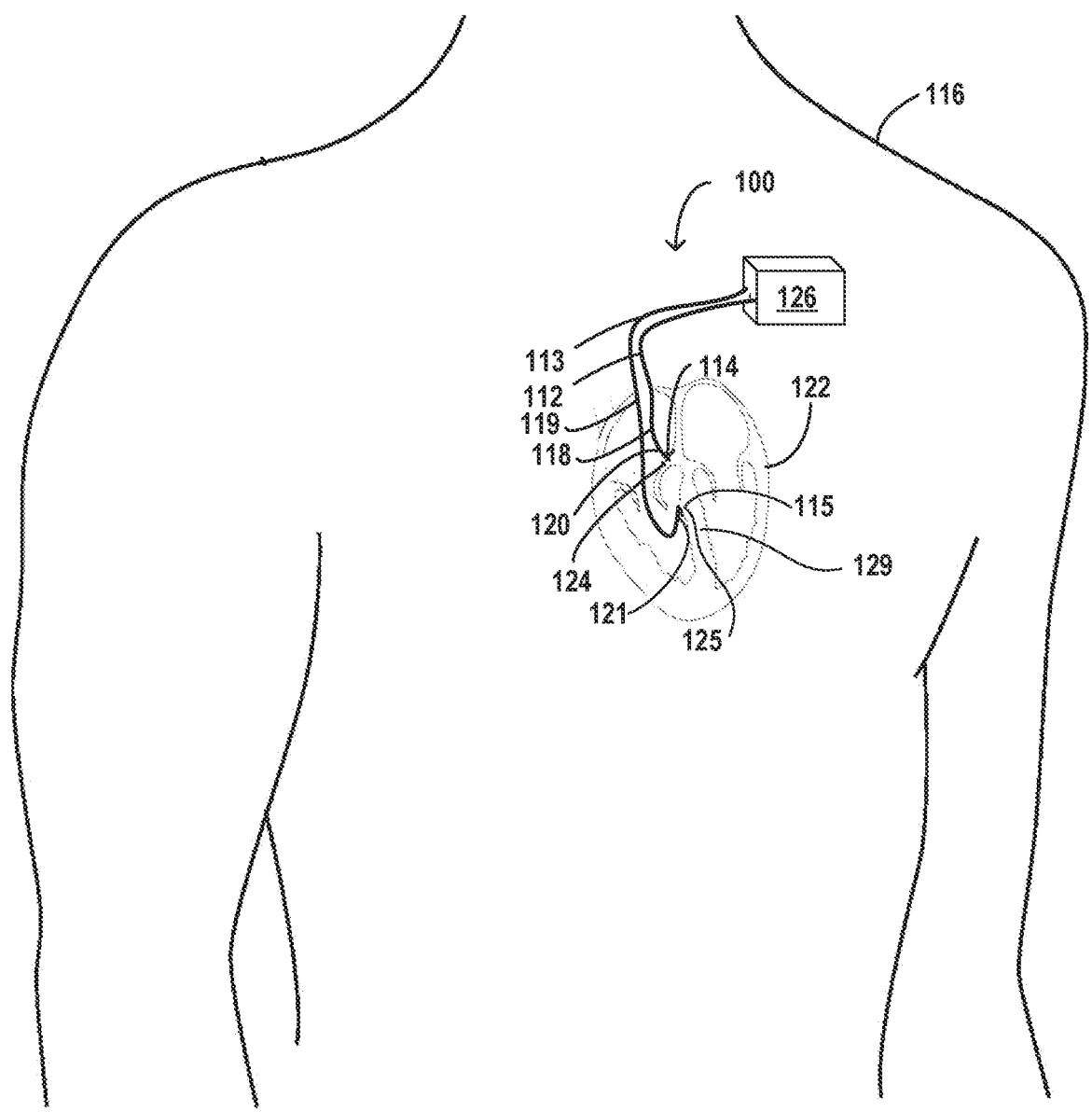
FIG. 1 is conceptual diagram illustrating an example implantable medical device system in accordance with one or more aspects of this disclosure.

FIG. 1 is a conceptual diagram illustrating a portion of an example implantable medical device system 100 in accordance with one or more aspects of this disclosure. Implantable medical device system 100 may function as a dual-chamber pacemaker that delivers conduction system pacing to a heart 122 of patient 116.

In the example of FIG. 1, implantable medical device system 100 includes implantable medical leads 112, 113 and an implantable medical device (IMD) 126. Implantable medical leads 112, 113 include elongated lead bodies 118, 119 with distal portions 120, 121, respectively. Distal portions 120, 121 of implantable medical leads 112, 113 are positioned at target sites 114, 115 within a heart 122 of a patient 116. Each of distal portions 120, 121 may include one or more electrodes.

Target site 114 may be located at an atrioventricular septal wall of a right atrium (RA) of heart 122. Target site 115 may be located at an interventricular septal wall of a right ventricle (RV) or left ventricle (LV) of heart 122. Each of leads 112, 113 may be a bipolar or multipolar lead.

A clinician may maneuver distal portions 120, 121 through the vasculature of patient 116 in order to position distal portions 120, 121 at or near target sites 114, 115. For example, the clinician may guide distal portion 120 through the superior vena cava (SVC) and into the RA, in order to access target site 114 on an atrioventricular septal wall 128 of heart 122, e.g., in the triangle of Koch region. The clinician may guide distal portion 121 through the SVC to target site 115 on or in a ventricular septal wall 129 of heart 122. In some examples, other pathways or techniques may be used to guide distal portions 120, 121 into other target implant sites within the body of patient 116. Implantable medical device system 100 may include a delivery catheter and/or outer member (not shown), and implantable medical leads 112, 113 may be guided and/or maneuvered within a lumen of the delivery catheter in order to approach target sites 114, 115.

In some examples, target site 114 may be the triangle of Koch region in the atrioventricular septal wall of the patient's heart, and target site 115 may be the ventricular septal wall in the basal (e.g., high basal or high septal) region or apical (e.g., low septal or near the apex) region. Implantation in the triangle of Koch region of the atrioventricular septal wall may facilitate pacing of the His bundle or ventricular myocardium. Implantation in the basal region of the ventricular septal wall may facilitate pacing of one or both of the His bundle branches. Implantation in the apical region may facilitate pacing of Purkinje fibers.

Implantable medical leads 112, 113 may include electrodes 124, 125 configured to penetrate cardiac tissue at or near target sites 114, 115, respectively. For example, electrode 125 of implantable medical lead 113 may be configured to penetrate to a position at or near the left bundle branch (LBB), His bundle (HB), right bundle branch (RBB), other specialized conductive tissue, or other ventricular tissue of heart 122. In examples where electrode 125 is configured to penetrate to a position at or near the LBB or HB, electrode 125 may traverse the ventricular septum from right to left. In some examples, electrodes 124, 125 are configured to function as electrodes in order to, for example, provide pacing to heart 122. Electrodes 124, 125 may be electrically connected to conductors (not shown) extending through implantable medical leads 112, 113 from electrodes 124, 125. In some examples, the conductors are electrically connected to therapy delivery circuitry of an implantable medical device (IMD) 126, with the therapy delivery circuitry configured to provide electrical signals through the conductor to electrodes 124, 125. Electrodes 124, 125 may conduct the electrical signals to the target tissue of heart 122, causing the cardiac muscle, e.g., of the ventricles, to depolarize and, in turn, contract at a regular interval. In examples in which one or more of electrodes 124, 125 penetrate to a position at or near the HB, RBB, LBB, or other specialized conductive tissue of heart 122, the cardiac pacing delivered via electrodes 124, 125 may be conduction system pacing (CSP) of heart 122, which may provide more physiologic activation and contraction of heart 122. Electrodes 124, 125 may also be connected to sensing circuitry of IMD 126 via the conductor, and the sensing circuitry may sense activity of heart 122 via electrode 124. Electrodes 124, 125 may have various shapes such as tines, helices, screws, rings, and so on.

In some examples, electrodes 124, 125 are configured to be extendable and/or retractable with respect to lead bodies 118, 119, in order to facilitate penetration of the cardiac tissue in the vicinity of target sites 114, 115. Lead bodies 118, 119 may allow electrodes 124, 125 to be placed deeper into the tissue and to provide multiple electrodes at different locations. The extension and/or retraction of electrodes 124, 125 may be controlled by a clinician. In some examples, another medical device capable of being electrically connected to implantable medical leads 112, 113 during implantation, such as a pacing system analyzer, may be configured to take electrical measurements during penetration of electrodes 124, 125 into the cardiac tissue in order to, for example, determine suitable locations within the cardiac tissue for CSP of heart 122.

In the example of FIG. 1, implantable medical device system 100 may implement a method for determining a patient-specific timing regime and may administer cardiac pacing to a native conduction system (e.g., at least one of the HB, LBB, or RBB) of heart 122 of patient 116 based on the patient-specific timing regime. In some instances, the native conduction system may be referred to as the "His-Purkinje conduction system" or "His-Purkinje system" which generally includes the HB, RBB, LBB and the Purkinje fibers. Example techniques for determining the patient-specific timing regime are described in detail below. A timing regime indicates times at which to apply pulses. The adaptive optimized pacing provided by implantable medical device system 100 may equal or exceed the clinical efficiency of conventional cardiac resynchronization therapy, but only uses two leads. In some examples, an implantable medical device system provides conduction system pacing as described herein using a single lead placed in the right atrium and including electrodes configured to pacing and sense the right atrium and the left ventricle or other ventricular conduction system components discussed above, e.g., ventricle from atrium (VfromA) pacing. Furthermore, although described primarily in the context of examples in an IMD and intravascular leads, one or more transcatheter pacing devices may be additionally or alternatively used in some examples.

Figure 2:
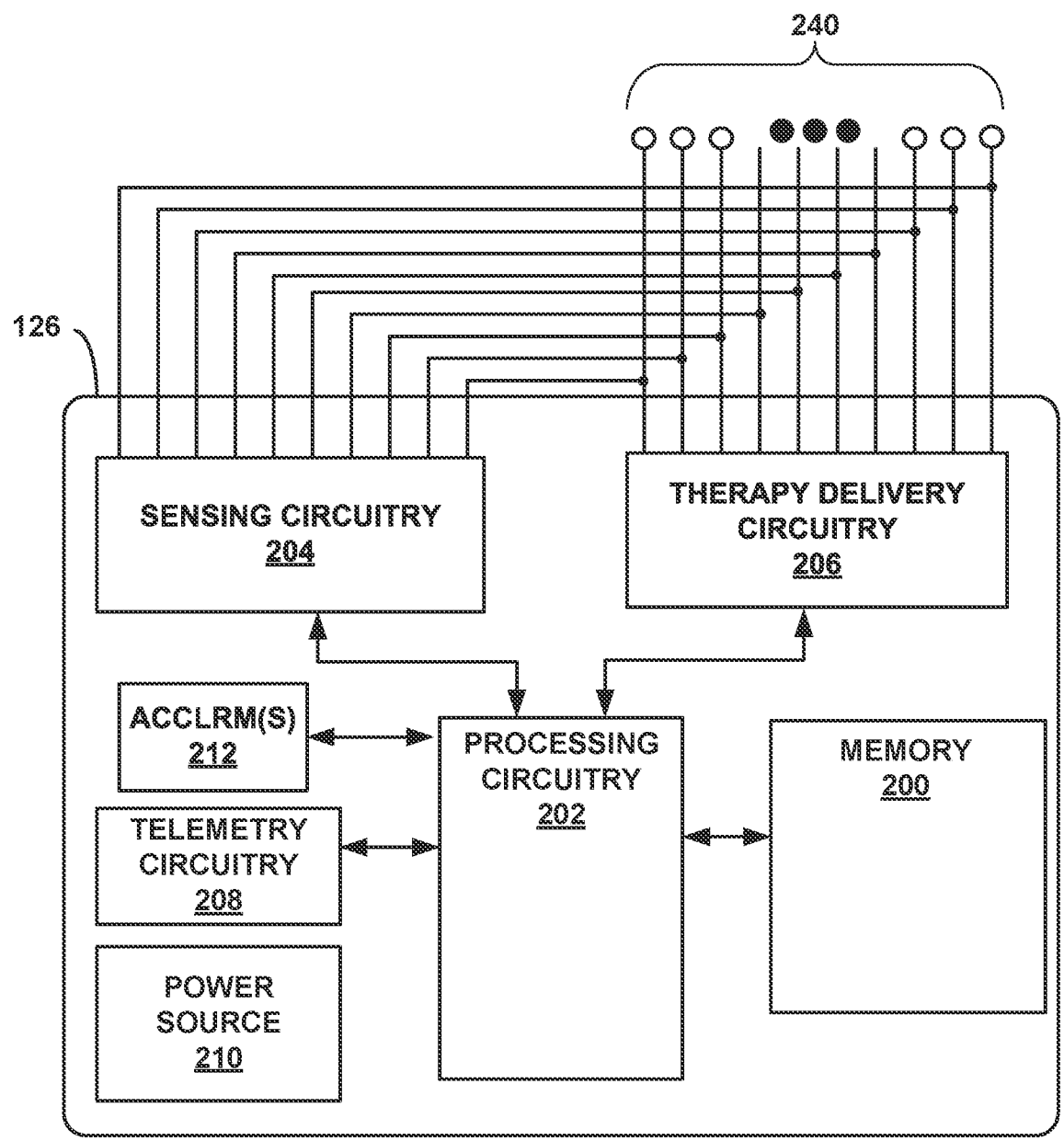
FIG. 2 is a functional block diagram of an example configuration of an implantable medical device in accordance with one or more aspects of this disclosure.

FIG. 2 is a functional block diagram of one example configuration of IMD 126 of FIG. 1 in accordance with one or more aspects of this disclosure. In the illustrated example, IMD 126 includes memory 200, processing circuitry 202, sensing circuitry 204, therapy delivery circuitry 206, telemetry circuitry 208, and power source 210, one or more of which may be disposed within housing 60 of IMD 126. In the example of FIG. 2, IMD 126 also includes one or more accelerometers 212. In some examples, memory 200 includes computer-readable instructions that, when executed by processing circuitry 202, cause IMD 126 and processing circuitry 202 to perform various functions attributed to IMD 126 and processing circuitry 202 herein. Memory 200 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 202 may include one or more of a microprocessor, a controller, digital signal processing circuitry (DSP), an application specific integrated circuit (ASIC), a field-programmable gate array (FPGA), or equivalent discrete or integrated logic circuitry. In some examples, processing circuitry 202 may include multiple components, such as any combination of one or more microprocessors, one or more controllers, one or more DSPs, one or more ASICs, or one or more FPGAs, as well as other discrete or integrated logic circuitry. The functions attributed to processing circuitry 202 herein may be implemented as software, firmware, hardware or any combination thereof. Processing circuitry 202 may be configured to determine a heart rate of heart 122 based on activity sensed by sensing circuitry 204 and determine a patient-specific timing regime. Processing circuitry 202 may control therapy delivery circuitry 206 to deliver pacing to a native conduction system of heart 122 based on the patient-specific timing regime, e.g., to provide cardiac resynchronization.

Sensing circuitry 204 is configured to monitor signals from at least one of electrodes 240 in order to monitor activity of heart 122, e.g., via electrogram (EGM) signals. For example, sensing circuitry 204 may sense atrial events (e.g., a P-wave) with one or more of electrodes 240 or sense an LV event (e.g., an R-wave) with other ones of electrodes 240. Electrodes 240 may correspond to electrodes, other electrodes on one or more leads, and/or one or more electrodes on a housing of IMD 126 In some examples, sensing circuitry 204 includes switching circuitry to select which of the available electrodes are used to sense the activity of heart 122. For example, processing circuitry 202 may select the electrodes that function as sense electrodes via the switching circuitry within sensing circuitry 204, e.g., by providing signals via a data/address bus. In some examples, sensing circuitry 204 includes one or more sensing channels, each of which may comprise an amplifier. In response to the signals from processing circuitry 202, the switching circuitry of sensing circuitry 204 may couple the outputs from the selected electrodes to one of the sensing channels.

In some examples, one channel of sensing circuitry 204 may include an R-wave amplifier that receives signals from one or more of electrodes 240, which are used for pacing and sensing in the RV of heart 122. Another channel may include another R-wave amplifier that receives signals from one or more of electrodes 240, which are used for pacing and sensing proximate to the LV of heart 122. In some examples, the R-wave amplifiers may take the form of an automatic gain controlled amplifier that provides an adjustable sensing threshold as a function of the measured R-wave amplitude of the heart rhythm.

In addition, in some examples, one channel of sensing circuitry 204 may include a P-wave amplifier that receives signals from one or more of electrodes 240, which are used for pacing and sensing in the RA of heart 122. In some examples, the P-wave amplifier may take the form of an automatic gain controlled amplifier that provides an adjustable sensing threshold as a function of the measured P-wave amplitude of the heart rhythm. Furthermore, in some examples, one or more of the sensing channels of sensing circuitry 204 may be selectively coupled to a housing electrode, or elongated electrodes, with or instead of one or more of other types of electrodes, e.g., for unipolar sensing of R-waves or P-waves in any chamber of heart 122.

Signals from the sensing electrodes may be converted to multi-bit digital signals by an analog-to-digital converter for storage in memory 200. Processing circuitry 202 may employ digital signal analysis techniques to characterize the digitized signals stored in memory 200 to detect and classify the patient's heart rhythm from the signals. Processing circuitry 202 may detect and classify the heart rhythm of patient 116 by employing any of the numerous signal processing methodologies known in the art.

Signals generated by sensing circuitry 204 may include, for example: an RA-event signal, which indicates a detection of a P-wave via electrodes positioned to sense activity of the RA; an LA-event signal that indicates a detection of a P-wave via electrodes positioned to sense activity of the LA; an RV-event signal that indicates a detection of an R-wave via electrodes positioned to sense activity of the RV; or an LV-event signal that indicates a detection of an R-wave via electrodes positioned to sense activity of the LV. In some examples, IMD 126 is not connected to electrodes that are implanted within the LA. In other examples, IMD 126 is connected to electrodes that are positioned to sense activity (e.g., electrical activity) of the LA.

In some examples, IMD 126 may include one or more additional sensors, such as accelerometers 212. In some examples, accelerometers 212 may comprise one or more three-axis accelerometers. Signals generated by accelerometers 212 may be indicative of, for example, gross body movement of patient 116, such as a patient posture or activity level. Regardless of the configuration of accelerometers 212, processing circuitry 202 may determine patient parameter values based on the signals obtained therefrom. Accelerometers 212 may produce and provide signals to processing circuitry 202 for a determination as to the posture and activity level of patient 116 at a given time. Processing circuitry 202 may then use the determined posture and activity level to further determine whether patient 116 is awake or asleep, and, if patient 116 is determined to be awake, to further determine whether patient 116 is at rest or exercising. Furthermore, in some examples, processing circuitry 202 may use signals generated by accelerometers 212 to sense specific cardiac events, such as atrial or ventricular contractions.

In the example of FIG. 2, therapy delivery circuitry 206 is electrically coupled to electrodes 240. Electrodes 124, 125 (FIG. 1) may include one or more of electrodes 240. Therapy delivery circuitry 206 is configured to administer cardiac pacing. For example, therapy delivery circuitry 206 may deliver a pacing stimulus to a native conduction system of heart 122 and thereby administer cardiac pacing.

Therapy delivery circuitry 206 may include switching circuitry. Processing circuitry 202 may use the switching circuitry to select, e.g., via a data/address bus, which of the available electrodes are used to deliver pacing pulses. The switching circuitry may include a switch array, switch matrix, multiplexer, or any other type of switching device suitable to selectively couple energy to selected electrodes. In other examples, processing circuitry 202 may select a subset of electrodes 240 with which energy is delivered to heart 122 without a switching circuitry.

Processing circuitry 202 implements an algorithm that determines a patient-specific optimal regime for conduction system pacing. As described in this disclosure, sensing circuitry 204 generates signals representing activity of heart 122 of patient 116. Processing circuitry 202 may determine, based on the signals, an intrinsic delay of the heart of patient 116. Processing circuitry 202 may also determine whether the intrinsic delay is indicative of a first-degree heart block being present in heart 122 of patient 116. Furthermore, processing circuitry 202 may determine the patient-specific timing regime for conduction system pacing based on whether the intrinsic delay is indicative of the first-degree heart block being present in the heart of the patient. Therapy delivery circuitry 206 may administer cardiac pacing to a native conduction system of heart 122 of patient 116 based on the patient-specific timing regime.

As noted above, processing circuitry 202 may determine a patient-specific timing regime for patient 116. As part of determining the patient-specific timing regime for patient 116, processing circuitry 202 may determine an intrinsic delay. To determine the intrinsic delay, processing circuitry 202 may configure therapy delivery circuitry 206 to periodically pause from ventricular pacing to measure an As to RVs time or an Ap to RVs time of patient 116. For example, processing circuitry 202 may configure therapy delivery circuitry 206 to skip one pace per minute or prolong the timing of AV pacing by up to 300 ms. The As to RVs time is an interval between an atrial sense event (As) and activation (e.g., the earliest onset of activation) of the right ventricle (RVs). An atrial sense event occurs when processing circuitry 202 detects an intrinsic depolarization of the right atrium. IMD 126 may use an electrode of lead 112 to detect an atrial sense event. The Ap to RVs time is an interval between an atrial pace event (Ap) and activation (e.g., earliest onset of activation) of the right ventricle (RVs). In some examples, processing circuitry 202 may determine RVs as an onset of a QRS block in a patient with left bundle branch block (LBBB). In some examples, processing circuitry 202 may determine RVs by sensing of electrical activity of the right ventricle via a right ventricle tip electrode of an RV lead (e.g., lead 125). In some examples, processing circuitry 202 may determine RVs by sensing the activation of the right ventricle of the heart of patient 116 using a far-field electrogram, e.g., using a coil-to-can EGM or atrial ring-to-can EGM.

This disclosure uses the term intrinsic delay to refer to either an As to RVs time or an Ap to RVs time. An atrial pace event (Ap) is an event in which an atrial pacing pulse was administered. Therapy delivery circuitry 206 may deliver the atrial pacing pulse via lead 112. In some examples, sensing circuitry 204 may detect RVs using a far-field electrogram, for example, as the beginning of the QRS complex.

Processing circuitry 202 may also periodically pace the right ventricle (e.g., via lead 113) with premature pacing (e.g., a single pace applied to the conduction system with an AV pace timing of 10 ms after the As or Ap, occurring once per hour), to measure the patient's "HV" time. For instance, in the context of FIG. 1, processing circuitry 202 may cause therapy delivery circuitry 206 to administer a pulse on lead 113, e.g., via electrode 125. In this disclosure, HV is the time between delivery of a conduction system pace and the onset (e.g., earliest onset) of ventricular activation, which may be detected in a far-field electrogram.

Additionally, processing circuitry 202 may determine whether patient 116 has normal AV conduction. Patient 116 may have abnormal AV conduction if patient 116 has first-degree heart block. Processing circuitry 202 may determine that patient 116 has normal AV conduction based on the intrinsic delay being less than a specific threshold. For instance, in an example where the intrinsic delay is the As to RVs time, processing circuitry 202 may determine that patient 116 has normal AV conduction when the As to RVs time is less than 220 ms. In an example where the intrinsic delay is the Ap to RVs time, processing circuitry 202 may determine that patient 116 has normal AV conduction when the Ap to RVs time is less than 250 ms. Processing circuitry 202 may determine that patient 116 does not have normal AV conduction otherwise.

In examples where the intrinsic delay is the As to RVs time and patient 116 has normal AV conduction (e.g., patient 116 does not have first-degree heart block), processing circuitry 202 may calculate AV pace timing as:

$$\text{minimum}(Y*(\text{As to RVs}),(\text{As to RVs})-\text{HV}) \quad (1)$$

In equation (1), the AV pace timing indicates the patient-specific timing regime and may be representative of a delay between an As event and delivery of a pace to the conduction system via 125.

In examples where the intrinsic delay is the Ap to RVs time and patient 116 has normal AV conduction, processing circuitry 202 may calculate AV pace timing as:

$$\text{minimum}(Y*(\text{Ap to RVs}),(\text{Ap to RVs})-\text{HV}) \quad (2)$$

In equation (2), the AV pace timing indicates the patient-specific timing regime and may be representative of a delay between an Ap event and delivery of a pace to the conduction system via 125.

In equations (1) and (2), Y is a fraction in the range of 0.4 to 0.8. In some examples, empirical measurements from a population of humans can be used to determine a best value of Y for a population, to ensure fusion between intrinsic activation of the RV and paced activation of the LV. In some examples, Y may be a programmable parameter. Patients with normal AV conduction already have AV synchrony. Equations (1) and (2) provide interventricular synchrony such that the conduction system pacing fuses with the remaining intrinsic activation of the ventricle. By determining the AV pace timing in this way, processing circuitry 202 determines a patient-specific timing regime for patient 116. Therapy delivery circuitry 206 may administer cardiac pacing to a native conduction system of heart 122 of patient 116 by generating pulses at intervals separated by the calculated AV pace timing (and thereby administering cardiac pacing in accordance with the patient-specific timing regime). In the context of FIG. 1, therapy delivery circuitry 206 may generate the pulses on lead 113 and therefore stimulate a portion of the native conduction system (e.g., left bundle branch or right bundle branch) of heart 122 of patient 116 in the septum between the left and right ventricles.

In examples where the intrinsic delay is the As to RVs time and patient 116 does not have normal AV conduction (e.g., patient 116 has first-degree heart block), processing circuitry 202 may calculate AV pace timing as:

$$\text{minimum}(\text{Pend}+X-\text{HV},\text{As to RVs}-\text{HV}) \quad (3)$$

In equation (3), the AV pace timing indicates the patient-specific timing regime and may be representative of a delay between an As event and delivery of a pace to the conduction system via 125. In another example, processing circuitry 202 may calculate AV pace timing as:

$$\text{minimum}(\text{Pend}+X,\text{As to RVs}-\text{HV}) \quad (3')$$

In examples where the intrinsic delay is the Ap to RVs time and patient 116 does not have normal AV conduction, processing circuitry 202 may calculate AV pace timing as:

$$\text{minimum}(\text{Pend}+X-\text{HV},\text{Ap to RVs}-\text{HV}) \quad (4)$$

In equation (4), the AV pace timing indicates the patient-specific timing regime and may be representative of a delay between an Ap event and delivery of a pace to the conduction system via 125. In another example, processing circuitry 202 may calculate AV pace timing as:

$$\text{minimum}(\text{Pend}+X\ \text{Ap to RVs}-\text{HV}) \quad (4')$$

In equations (3) and (4), X is a programmable value (standard value may be in a range of approximately 50-80 ms) and Pend denotes a time from As to an end of a P-wave (in the case of equation (3) and Ap to an end of a P-wave (in the case of equation (4)) that may be periodically measured in a far-field electrogram. In equations (3') and (4'), a standard value of X may be in a range of approximately 30-70 ms).

In some examples, implantable medical device system 100 seeks both the restoration of AV synchrony (specifically left atrium to left ventricle synchrony) and fusion of left ventricular and right ventricular activation. In examples where a bipolar lead (e.g., lead 113 (FIG. 1) is positioned for left bundle branch area pacing (LBBAP), the bipolar lead may include a ventricular tip electrode and a ventricular ring electrode. If the ventricular ring electrode is capable of pacing the right bundle (via right bundle branch area pacing (RBBAP)), therapy delivery circuitry 206 may deliver paces simultaneously to the ventricular tip electrode (thereby pacing the LBB) and the ventricular ring electrode (thereby pacing the RBB) at an AV pace timing according to Equations (3) or (4). Therapy delivery circuitry 206 may administer cardiac pacing to a native conduction system of heart 122 of patient 116 by generating pulses at intervals separated by the calculated AV pace timing (and thereby administer cardiac pacing in accordance with the patient-specific timing regime).

Once pacing has begun according to the above algorithm, sensing circuitry 204 may measure the time from atrial sense (As) or atrial pace (Ap) to the end of a paced QRS complex (e.g., as determined from a far-field electrogram like Atrial Ring to Can or Ventricular Ring to Can), to establish a baseline expectation for an As (or Ap) to QRS end interval. If a subsequent measurement of the As (or Ap) to QRS end interval produces a longer As (or Ap) to QRS end interval, this may indicate loss of AV and/or interventricular synchrony. Accordingly, processing circuitry 202 may adjust pace timing to attempt to restore the expected As (or Ap) to QRS interval. For example, processing circuitry 202 may repeat the above procedure (measuring As to RVs, Ap to RVs, Pend, and HV) to compute a new patient-specific timing regime. In some examples, processing circuitry 202 may determine a QRS width based on a far-field electrogram. Increasing QRS width indicates that something has changed and processing circuitry 202 may repeat the above procedure to computing a new patient-specific timing regime.

Left bundle branch block (LBBB) is a condition in which activation of the left ventricle of the heart is delayed relative to the right ventricle. LBBB is a form of interventricular dyssynchrony. Therapy delivery circuitry 206 may administer left bundle branch (LBB) pacing to address LBBB. Therapy delivery circuitry 206 may administer LBB pacing in accordance with the patient-specific timing regime. LBBB may be intermittent or dependent on the heart rate of patient 116 In examples where implantable medical device system 100 administers LBB pacing according to the patient-specific timing regime, therapy delivery circuitry 206 may temporarily prolong the As to ventricular pacing time (SAV) or Ap to ventricular pacing timing (PAV) or pause from pacing (e.g., once per minute or hour) to measure the intrinsic delay of patient 116 (e.g., the patient's As to RVs time or Ap to RVs time). When temporarily prolonging SAV or PAV or pausing pacing to measure the intrinsic delay, processing circuitry 202 may determine, based on the intrinsic delay and/or via sensing LBB activation or via electrogram morphology processing, that patient 116 does not have left bundle branch block (LBBB) and left bundle pacing is not needed at this time. An example operation of implantable medical device system 100 in which left bundle pacing may be suspended is described in FIG. 5. IMD 126 may thus reduce energy consumption by avoiding ventricular pacing when the ventricular conduction system of patient 116 is functioning. Because left bundle branch block can be heart rate dependent, the feature of determining whether left bundle pacing is needed may depend on some combination of the observed heart rate and the once-per-minute determination of LBB conduction as described above. After cessation of LBB pacing, processing circuitry 202 can monitor signals generated by sensing circuitry 204 for the occurrence of intrinsic ventricular activation (i.e., ventricular activation caused by the heart's own timing signals) within a reasonable intrinsic delay following each atrial sense event. If a prolonged intrinsic delay is detected (i.e., if the intrinsic delay is greater than a specific threshold) or if a block (e.g., an LBBB) is otherwise detected, processing circuitry 202 can revert to LBB pacing. Thus, in accordance with the examples of this disclosure, processing circuitry 202 may switch a mode for pace timing based on observation of first-degree heart block, QRS duration, or LBBB occurrence.

In some examples, processing circuitry 202 may store diagnostic data in memory 200. The diagnostic data may include one or more of a percentage of conduction system pacing, the measured HV, As to RVs, Ap to RVs, As to QRS end or Ap to QRS end. The percentage of conduction system pacing may indicate a percentage of time that therapy delivery circuitry 206 administers cardiac pacing (e.g., CRT) to a native conduction system of heart 122 of patient 116. In some examples, the percentage of conduction system pacing indicates a percentage of beats on which therapy delivery circuitry 206 administers cardiac pacing (e.g., CRT) to a native conduction system of heart 122 of patient 116. As to QRS end denotes a time duration from an As event to an end of a QRS complex. Ap to QRS end denotes a time duration from an Ap event to an end of the QRS complex. The diagnostic data may be used to detect the occurrence and/or burden of abnormal cardiac conditions.

In some examples, processing circuitry 202 may determine pace timing by mechanical assessment of cardiac activation. For instance, implantable medical device system 100 may include one or more transcatheter pacing devices, which may also be referred to as transcatheter pacemakers, intracardiac pacemakers, or leadless pacemakers. An example type of transcatheter pacing device is a Micra™ device from Medtronic, Inc of Minneapolis, Minnesota. In such examples, IMD 100 of FIG. 1 may be a transcatheter pacing device and may be positioned inside heart 122 instead of outside heart 122 as shown in the example of FIG. 1. The transcatheter pacing device has at least one 3-D accelerometer (e.g., accelerometers 212 of FIG. 2) that can detect atrial contraction "atrial kick" as well as ventricular contraction. Thus, in some examples, accelerometers 212 may be included in or considered to be part of sensing circuitry (e.g., sensing circuitry 204) that generates signals representing activity of heart 122 of patient 116. The transcatheter pacing device may include a modified cathode electrode that is positioned either in the right ventricle or in the right atrium such that a pacing cathode is capable of pacing the native conduction system of heart 122. For example, the electrode may be positioned in the right atrium and may be long enough to reach tissue (e.g., His bundle or another portion of the native conduction system of heart 122) that controls activation of one or more of the ventricles. This includes the aforementioned "VfromA" pacing.

In examples where IMD 126 is a transcatheter pacing device, therapy delivery circuitry 206 may periodically pause from pacing to assess the time between atrial mechanical activation (Am) and ventricular mechanical activation (Vm) to determine a mechanical AV interval (Am to Vm). In some examples, the transcatheter pacing device also periodically delivers a premature pace to the conduction system (e.g., delivered immediately upon detection of atrial mechanical activation or delivered during diastole), to determine the time between conduction system pacing and ventricular mechanical activation (H to Vm). Subsequently, the transcatheter pacing device may operate continuously by sensing atrial mechanical activation and then pacing the conduction system at a time (Am to Vm)−(H to Vm)+x after sensing the atrial mechanical activation, where x is a programmable factor. In some examples, x is programmable. In some examples, x is determined for a population. This may result in synchrony between native ventricular activation and paced activation. After normal pacing has begun, the transcatheter pacing device may monitor the time from Am to Vm during pacing, to determine if dyssynchrony has developed which may require modification of pace timing. In some examples, the transcatheter pacing device may monitor the time from Am to Vm once per minute (or other time period) to determine if dyssynchrony has developed.

Figure 3:
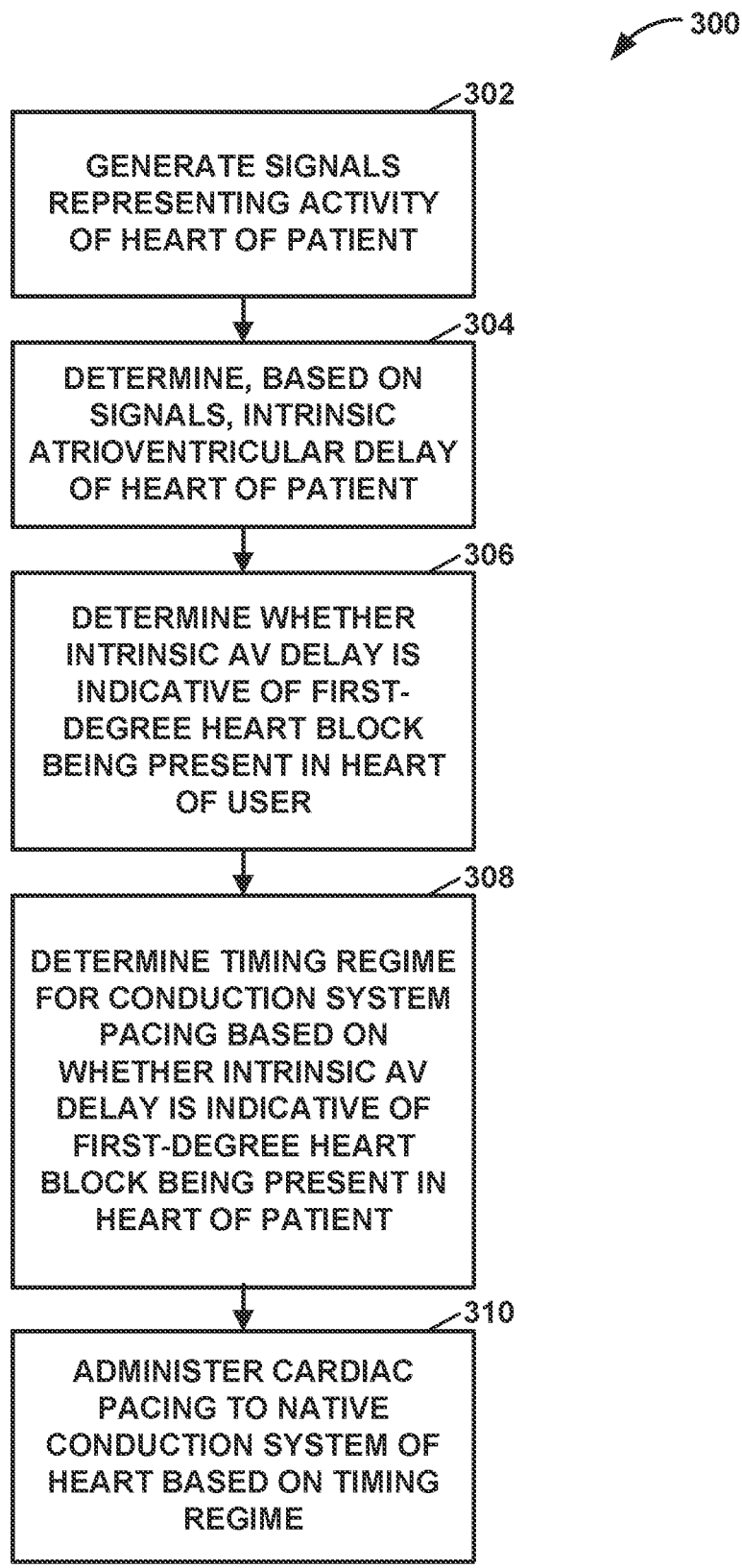
FIG. 3 is a flowchart illustrating an example method for administering cardiac pacing to a native conduction system of a heart of a patient, in accordance with one or more aspects of this disclosure.

FIG. 3 is a flowchart illustrating an example method 300 for administering cardiac pacing to a native conduction system of heart 122 of patient 116, in accordance with one or more aspects of this disclosure. The flowcharts of this disclosure are provided as examples. In other examples, more, fewer, or different actions may be performed, or actions may be performed in different orders or certain actions may be performed in parallel.

In the example of FIG. 3, sensing circuitry 204 may generate signals representing activity of heart 122 of patient 116 (302). The activity may include electrical activity of heart 122. In some examples, the activity may include physical motions of heart 122, e.g., as measured by one or more accelerometers of sensing circuitry 204.

Processing circuitry 202 may determine, based on the signals, an intrinsic delay of the heart of the patient (304). For example, processing circuitry 202 may determine the intrinsic delay as an As to RVs time or an Ap to RVs time. In some examples where the cardiac pacing administered by implantable medical device system 100 is ventricular pacing and processing circuitry 202 is determining the intrinsic delay, therapy delivery circuitry 206 may pause the ventricular pacing. While the ventricular pacing is paused, processing circuitry 202 may determine, based on signals generated by sensing circuitry 204, the intrinsic delay as one of: a time between sensing of a depolarization of a right atrium of the heart of the patient and an activation (e.g., earliest onset of activation) of a right ventricle of the heart of the patient (e.g., an As to RVs time) or a time between an atrial pace event of the right atrium of the heart of the patient and the activation (e.g., earliest onset of activation) of the right ventricle of the heart of the patient (e.g., an Ap to RVs time). In some examples, processing circuitry 202 may determine the activation (e.g., earliest onset of activation) of the right ventricle of heart 122 of patient 116 using a far-field electrogram.

Furthermore, processing circuitry 202 may determine whether the intrinsic delay is indicative of a first-degree heart block being present in the heart of the patient (306). For instance, processing circuitry 202 may determine whether the intrinsic delay is greater than a threshold (e.g., 220 ms for As to RVs or 250 ms for Ap to RVs). Sensing circuitry 204 may generate signals representing activity of the heart of the patient while ventricular pacing is paused. Processing circuitry 202 may, in some examples, determine the intrinsic delay based on the signals representing activity of the heart of the patient while ventricular pacing is paused. In some such examples, processing circuitry 202 may determine whether the intrinsic delay is indicative of the first-degree heart block being present in the heart of the patient while ventricular pacing is paused.

Processing circuitry 202 may then determine a patient-specific timing regime for conduction system pacing based on whether the intrinsic delay is indicative of the first-degree heart block being present in the heart of the patient (308). In some examples, to determine the patient-specific timing regime, therapy delivery circuitry 206 may administer a pacing pulse to the native conduction system of heart 122 of patient 116. The pacing pulse may be a premature pacing pulse. In other words, the pacing pulse may come before therapy delivery circuitry 206 would normally administer a pacing pulse. Additionally, processing circuitry 202 may determine a pace-activation delay (HV) based on the signals generated by sensing circuitry 204. The pace-activation delay indicates a time between delivery of the pacing pulse and the onset (e.g., earliest onset) of ventricular activation. The onset of ventricular activation may be caused by the pacing pulse (e.g., premature pacing pulse) administered by therapy delivery circuitry 206.

For instance, to determine the patient-specific timing regime, processing circuitry 202 may determine that the intrinsic delay is indicative of the first-degree heart block being present in heart 122 of patient 116 based on whether the intrinsic delay is less than a threshold (e.g., 220 ms for As to RVs or 250 ms for Ap to RVs). For instance, processing circuitry 202 may determine that the intrinsic delay is not indicative of the first-degree heart block being present in heart 122 of patient 116 when the intrinsic delay is less than the threshold and may determine that the intrinsic delay is indicative of the first-degree heart block being present in heart 122 of patient 116 when the intrinsic delay is greater than the threshold. Based on the intrinsic delay not being indicative of the first-degree heart block being present in heart 122 of patient 116, processing circuitry 202 may determine the patient-specific timing regime based on a minimum of: (i) a coefficient multiplied by the intrinsic delay, and (ii) a difference between the intrinsic delay and the pace-activation delay (e.g., using equations (1) or (2)). However, if processing circuitry 202 determines that the intrinsic delay is indicative of the first-degree heart block being present in heart 122 of patient 116, processing circuitry 202 may determine the patient-specific timing regime based on a minimum of: (i) a sum of a delay between an atrial sense event or an atrial pacing event and an end of a P-wave of the heart and a programmable value minus the pace-activation delay, and (ii) a difference between the intrinsic delay and the pace-activation delay (e.g., using equations (3) or (4)). In this way, processing circuitry 202 may determine the patient-specific timing regime for conduction system pacing based on whether the intrinsic delay is indicative of the first-degree heart block being present in the heart of the patient, and in at least some instances, based on the intrinsic delay itself.

Therapy delivery circuitry 206 of implantable medical device system 100 may administer cardiac pacing to a native conduction system of heart 122 of patient 116 based on the patient-specific timing regime (310). In this way, processing circuitry 202 may control administration of cardiac pacing to a native conduction system of the heart of patient 116 based on the patient-specific timing regime. For example, therapy delivery circuitry 206 may generate pacing pulses via lead 112 or 113 (FIG. 1) in accordance with the patient-specific timing regime. In other examples, lead 112 could provide ventricular conduction system pacing if an electrode is positioned to pace the His bundle area (i.e., in a case of VfromA pacing). In some examples, processing circuitry 202 determines the patient-specific timing regime in terms of an intrinsic delay.

Figure 4:
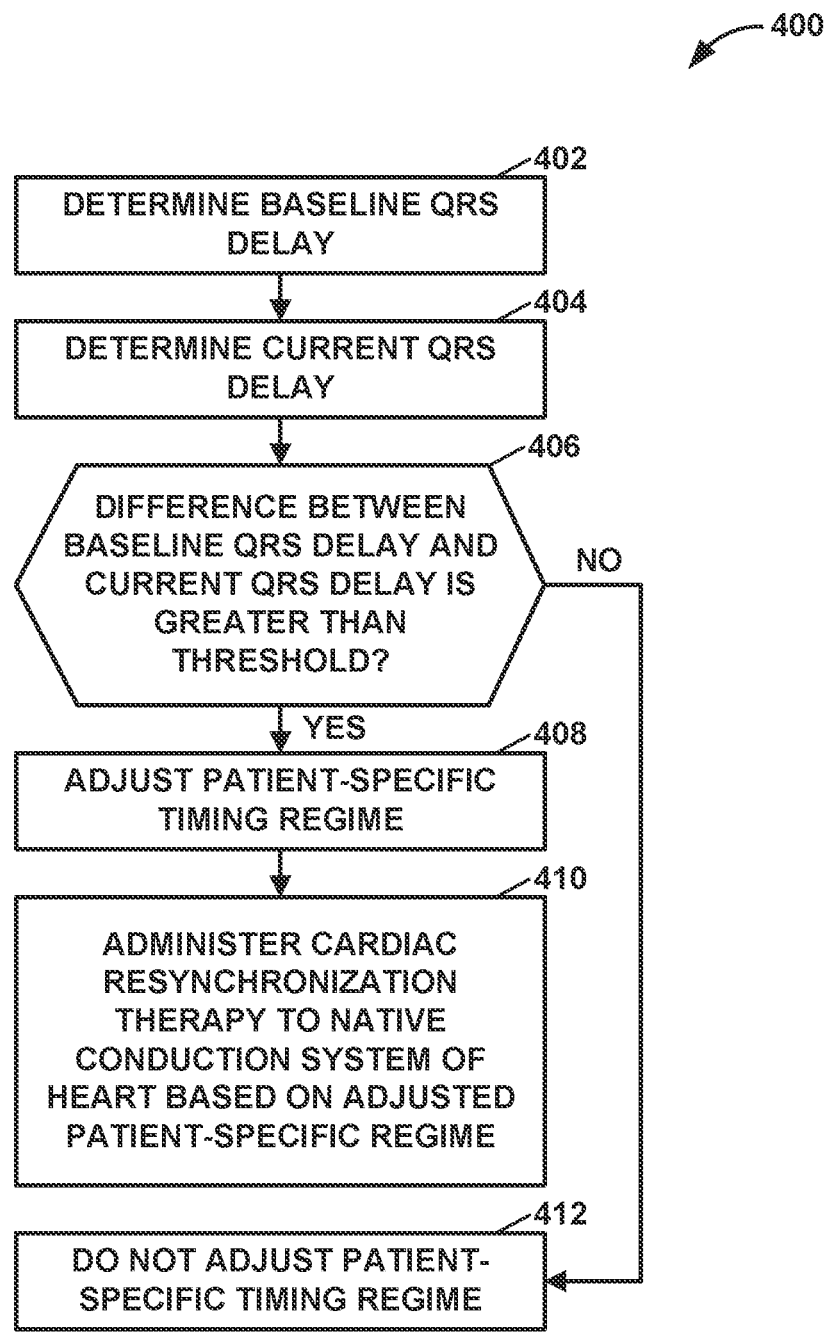
FIG. 4 is a flowchart illustrating an example method for determining an adjusted patient-specific timing regime in accordance with one or more aspects of this disclosure.

FIG. 4 is a flowchart illustrating an example method 400 for determining an adjusted patient-specific timing regime in accordance with one or more aspects of this disclosure. As noted above, loss of AV synchrony or interventricular synchrony may occur even when cardiac pacing is being administered by implantable medical device system 100. Accordingly, implantable medical device system 100 may adjust the patient-specific timing regime to restore AV and/or interventricular synchrony.

Accordingly, in the example of FIG. 4, processing circuitry 202 may determine a baseline QRS delay based on signals generated by sensing circuitry 204 (402). The baseline QRS delay is based on a set of determined differences in time between an atrial sense (As) event or an atrial pace (Ap) event to an end of a QRS complex. For example, processing circuitry 202 may determine the baseline QRS delay as an average of the determined differences, median of the determined differences, minimum of the determined differences, maximum of the determined differences, distribution of the determined differences, or otherwise determine the baseline QRS delay based on the determined differences.

Additionally, processing circuitry 202 may determine a current QRS delay based on the signals (404). The current QRS delay may be a difference in time between a current atrial sense (As) event or a current atrial pace (Ap) event and an end of a current QRS complex. In some examples, processing circuitry 202 may determine the current QRS delay based on multiple recent As or Ap events and ends of QRS complexes.

Furthermore, in the example of FIG. 4, processing circuitry 202 may determine whether a difference between the current QRS delay and the baseline QRS delay is greater than a threshold (406). Example values of the threshold may range from 10 to 40 milliseconds.

If the difference between the current QRS delay and the baseline QRS delay is greater than the threshold ("YES" branch of 406), processing circuitry 202 may adjust the patient-specific timing regime, e.g., as described below (408). Therapy delivery circuitry 206 may subsequently administer cardiac pacing to the native conduction system of heart 122 of patient 116 based on the adjusted timing regime (410). Otherwise, if the difference between the current QRS delay and the baseline QRS delay is not greater than the threshold ("NO" branch of 406), processing circuitry 202 does not adjust the patient-specific timing regime (412). In other examples, processing circuitry 202 may also automatically determine that a change has occurred in the QRS delay by using statistical process control. In such examples, processing circuitry 202 maintains statistics regarding a normal QRS delay and normal variation. When the observed QRS delay exceeds the established expected distribution of QRS delays, processing circuitry 202 detects a change and therefore may adjust the patient-specific timing regime.

Processing circuitry 202 may adjust the patient-specific timing regime in one or more ways. For instance, in some examples, processing circuitry 202 may perform the method shown in the example of FIG. 3 to adjust the patient-specific timing regime. Thus, in this example, processing circuitry 202 may determine, based on signals generated by sensing circuitry 204, a second intrinsic delay of the heart of the patient; determine whether the second intrinsic delay is indicative of the first-degree heart block is present in the heart of the patient; determine, a second patient-specific timing regime for conduction system pacing based on the second intrinsic delay and whether the second intrinsic delay is indicative of the first-degree heart block being present in the heart of the patient; and therapy delivery circuitry 206 may administer cardiac pacing to a native conduction system of the heart of the patient based on the second patient-specific timing regime. In other examples, processing circuitry 202 may scan through AV delays, measuring the QRS delay after each pace, to minimize the QRS delay. For example, processing circuitry 202 may change the AV delay on a series of 7 beats by −30, −20, −10, 0, +10, +20, +30 ms, and determine which results in the smallest AV delay. Processing circuitry 202 may repeat this several times and take the average or repeat several beats at each setting before moving on.

Figure 5:
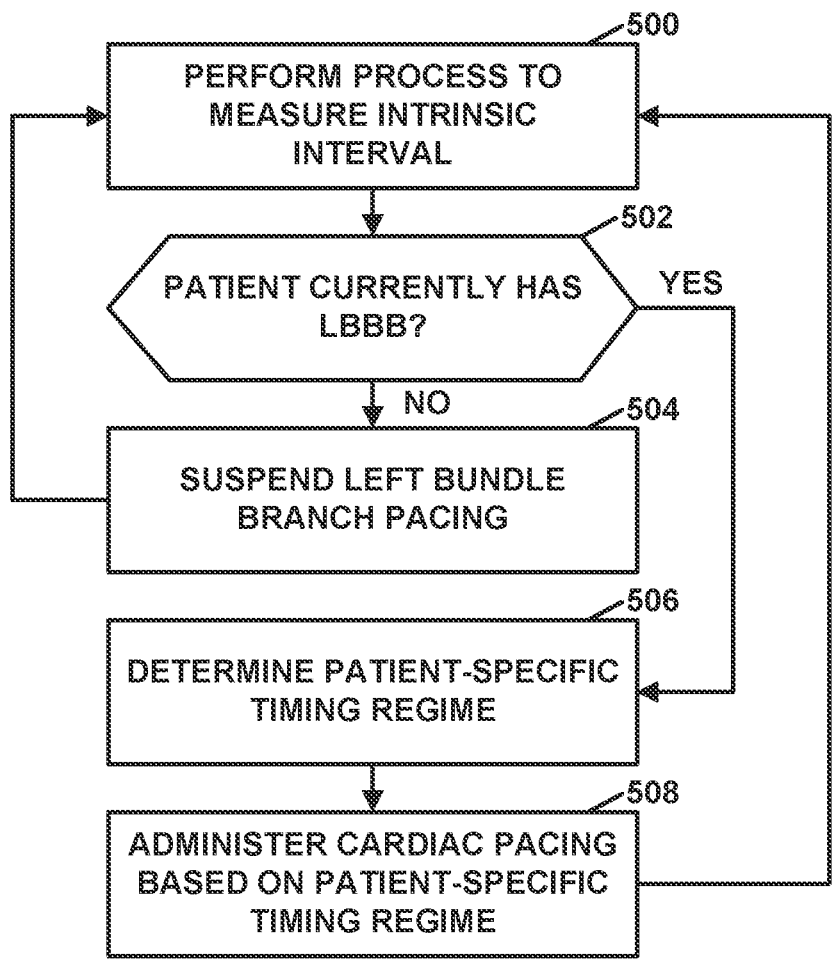
FIG. 5 is a flowchart illustrating an example operation of an implantable medical device system in which left bundle pacing may be suspended, in accordance with one or more techniques of this disclosure.

FIG. 5 is a flowchart illustrating an example operation of implantable medical device system 100 in which left bundle pacing may be suspended, in accordance with one or more techniques of this disclosure. In the example of FIG. 5, implantable medical device system 100 may perform a process to measure the intrinsic interval of patient 116 (500). For example, processing circuitry 202 may cause therapy delivery circuitry 206 to periodically prolong SAV or PAV or pause pacing to measure the As to RVs time or Ap to RVs time. During the prolongation or pause, processing circuitry 202 may determine whether patient 116 currently has LBBB (502). In other words, processing circuitry 202 may determine whether LBBB is present in heart 122 of patient 116. As noted above, LBBB may be intermittent or LBBB may be dependent on the current heart rate of patient 116. In some examples, processing circuitry 202 determines whether patient 116 currently has LBBB based on sensing (e.g., based on signals from sensing circuitry 204) left bundle branch activation. In some examples, processing circuitry 202 determines whether patient 116 currently has LBBB based on electrogram processing (e.g., determining a prolonged As to QRS end interval in combination with other parameters, such as ventricular sensing time). For instance, processing circuitry 202 may determine that patient 116 has LBBB when a time from the beginning of a QRS interval to the end of the QRS interval is greater than a threshold and the time from the beginning of the QRS interval to a right ventricular sense event is within a predetermined range (e.g., 10 ms to 15 ms).

In response to determining that patient 116 does not currently have LBBB ("NO" branch of 502), processing circuitry 202 may cause therapy delivery circuitry 206 to temporarily suspend left bundle branch pacing (504). In some examples, in response to determining that patient 116 does not currently have LBBB ("NO" branch of 502), processing circuitry 202 may also or alternatively cause therapy delivery circuitry 206 to extend SAV or PAV to allow intrinsic activation to occur. By extending SAV or PAV, therapy delivery circuitry 206 may deliver pacing shortly after a new block develops. Subsequently, implantable medical device system 100 may again perform the process to measure the intrinsic interval of patient 116 (500), e.g., after expiration of 1 minute. On the other hand, if patient 116 currently has LBBB ("YES" branch of 502), processing circuitry 202 may determine the patient-specific timing regime, e.g., as described elsewhere in this disclosure (506). Therapy delivery circuitry 206 may administer cardiac pacing (e.g., left bundle branch pacing) based on the patient-specific timing regime (508). Subsequently, implantable medical device system 100 may again perform the process to measure the intrinsic interval of patient 116 (500), e.g., after expiration of 1 minute. Furthermore, because LBBB may be dependent on the patient's heart rate, implantable medical device system 100 may again perform the process to measure the intrinsic interval of patient 116 (500) in response to detecting heart rates above or below one or more thresholds.

The following is a non-limiting list of examples that are in accordance with one or more techniques of this disclosure.

Example 1: A method includes generating, by sensing circuitry of an implantable medical device system, signals representing activity of a heart of a patient; determining, by processing circuitry of the implantable medical device system, based on the signals, an intrinsic delay of the heart of the patient; determining, by the processing circuitry, whether the intrinsic delay is indicative of a first-degree heart block being present in the heart of the patient; determining, by the processing circuitry, a patient-specific timing regime for conduction system pacing based on whether the intrinsic delay is indicative of the first-degree heart block being present in the heart of the patient; and administering, by therapy delivery circuitry of the implantable medical device system, cardiac pacing to a native conduction system of the heart of the patient based on the patient-specific timing regime.

Example 2: The method of example 1, wherein: administering the cardiac pacing comprises administering ventricular pacing, generating the signals comprises generating, by the sensing circuitry, signals representing activity of the heart of the patient while ventricular pacing is paused; determining the intrinsic delay comprises determining, by the processing circuitry, based on the signals representing activity of the heart of the patient while ventricular pacing is paused, the intrinsic delay as one of: a time between sensing of a depolarization of a right atrium of the heart of the patient and an activation of a right ventricle of the heart of the patient, or a time between an atrial pace event of the right atrium of the heart of the patient and the activation of the right ventricle of the heart of the patient.

Example 3: The method of any of examples 1-2, further comprising determining, by the processing circuitry, the activation of the right ventricle of the heart of the patient using a far-field electrogram.

Example 4: The method of any of examples 1-3, wherein the cardiac pacing comprises left bundle branch pacing and the method further comprises, based on left bundle branch block not being present in the heart of the patient, suspending, by the therapy delivery circuitry, the left bundle branch pacing.

Example 5: The method of any of examples 1-5, wherein determining whether the first-degree heart block is present comprises determining, by the processing circuitry, whether the intrinsic delay is greater than a threshold.

Example 6: The method of any of examples 1-5, wherein: the method further comprises: administering, by the therapy delivery circuitry, a pacing pulse to the native conduction system of the heart of the patient; and determining, by the processing circuitry, a pace-activation delay based on the signals, wherein the pace-activation delay indicates a time between delivery of the pacing pulse and an earliest onset of ventricular activation, and determining the patient-specific timing regime comprises determining, by the processing circuitry, the patient-specific timing regime based on the intrinsic delay, whether the intrinsic delay is indicative of the first-degree heart block being present in the heart of the patient, and the pace-activation delay.

Example 7: The method of example 6, wherein the pacing pulse is a premature pacing pulse.

Example 8: The method of any of examples 6-7, wherein determining the patient-specific timing regime comprises: determining, by the processing circuitry, whether the intrinsic delay is indicative of the first-degree heart block being present in the heart of the patient based on whether the intrinsic delay is less than a threshold; and based on the intrinsic delay not being indicative of the first-degree heart block being present in the heart of the patient, determining, by the processing circuitry, the patient-specific timing regime based on a minimum of: (i) a coefficient multiplied by the intrinsic delay, and (ii) a difference between the intrinsic delay and the pace-activation delay.

Example 9: The method of any of examples 6-7, wherein determining the patient-specific timing regime comprises: determining, by the processing circuitry, whether the intrinsic delay is indicative of the first-degree heart block being present in the heart of the patient based on whether the intrinsic delay is greater than a threshold; and based on the intrinsic delay being indicative of the first-degree heart block being present in the heart of the patient, determining, by the processing circuitry, the patient-specific timing regime based on a minimum of: (i) a sum of a delay between an atrial sense event or an atrial pacing event and an end of a P-wave of the heart and a programmable value minus the pace-activation delay, and (ii) a difference between the intrinsic delay and the pace-activation delay.

Example 10: The method of any of examples 1-9, further includes determining, by the processing circuitry, a baseline QRS delay based on the signals, wherein the baseline QRS delay is based on a set of determined differences in time between an atrial sense event or an atrial pace event to an end of a QRS complex; determining, by the processing circuitry, a current QRS delay based on the signals, wherein the current QRS delay is a difference in time between a current atrial sense event or a current atrial pace event and an end of a current QRS complex; determining, by the processing circuitry, whether a difference between the current QRS delay and the baseline QRS delay is greater than a threshold; and based on the difference between the current QRS delay and the baseline QRS delay being greater than the threshold: adjusting, by the processing circuitry, the patient-specific timing regime; and administering, by the therapy delivery circuitry, the cardiac pacing to the native conduction system of the heart of the patient based on the adjusted timing regime.

Example 11: The method of example 10, wherein adjusting the patient-specific timing regime comprises: determining, by the processing circuitry, based on the signals, a second intrinsic delay of the heart of the patient; determining, by the processing circuitry, whether the second intrinsic delay is indicative of the first-degree heart block being present in the heart of the patient; determining, by the processing circuitry, a second patient-specific timing regime for conduction system pacing based on the second intrinsic delay and whether the second intrinsic delay is indicative of the first-degree heart block being present in the heart of the patient; and administering, by the therapy delivery circuitry, the cardiac pacing to the native conduction system of the heart of the patient based on the second patient-specific timing regime.

Example 12: The method of any of examples 1-11, wherein determining the patient-specific timing regime for conduction system pacing comprises determining the patient-specific timing regime for conduction system pacing based on the intrinsic delay and whether the intrinsic delay is indicative of the first-degree heart block being present in the heart of the patient.

Example 13: An implantable medical device system includes sensing circuitry configured to generate signals representing activity of a heart of a patient; processing circuitry configured to: determine, based on the signals, an intrinsic delay of the heart of the patient; determine whether the intrinsic delay is indicative of a first-degree heart block being present in the heart of the patient; and determine a patient-specific timing regime for conduction system pacing based on whether the intrinsic delay is indicative of the first-degree heart block being present in the heart of the patient; and therapy delivery circuitry configured to administer cardiac pacing to a native conduction system of the heart of the patient based on the patient-specific timing regime.

Example 14: The system of example 13, wherein: the cardiac pacing comprises ventricular pacing, the sensing circuitry is configured such that, as part of generating the signals, the sensing circuitry generate signals representing activity of the heart of the patient while ventricular pacing is paused; the processing circuitry is configured such that, as part of determining the intrinsic delay, the processing circuitry determines, based on the signals representing activity of the heart of the patient while ventricular pacing is paused, the intrinsic delay as one of: a time between sensing of a depolarization of a right atrium of the heart of the patient and an activation of a right ventricle of the heart of the patient, or a time between an atrial pace event of the right atrium of the heart of the patient and the activation of the right ventricle of the heart of the patient.

Example 15: The system of any of examples 13-14, wherein the processing circuitry is further configured to determine the activation of the right ventricle of the heart of the patient using a far-field electrogram.

Example 16: The system of any of examples 13-15, wherein the cardiac pacing comprises left bundle branch pacing and the therapy delivery circuitry is configured to suspend, based on left bundle branch block not being present in the heart of the patient, the left bundle branch pacing.

Example 17: The system of any of examples 13-16, wherein the processing circuitry is configured such that, as part of determining whether the first-degree heart block is present, the processing circuitry determines whether the intrinsic delay is greater than a threshold.

Example 18: The system of any of examples 13-17, wherein: the therapy delivery circuitry is further configured to administer a pacing pulse to the native conduction system of the heart of the patient, the processing circuitry is configured to determine a pace-activation delay based on the signals, wherein the pace-activation delay indicates a time between delivery of the pacing pulse and an earliest onset of ventricular activation, and the processing circuitry is configured such that, as part of determining the patient-specific timing regime, the processing circuitry determines the patient-specific timing regime based on the intrinsic delay, whether the intrinsic delay is indicative of the first-degree heart block being present in the heart of the patient, and the pace-activation delay.

Example 19: The system of example 18, wherein the pacing pulse is a premature pacing pulse.

Example 20: The system of any of examples 18-19, wherein the processing circuitry is configured such that, as part of determining the patient-specific timing regime, the processing circuitry: determines whether the intrinsic delay is indicative of the first-degree heart block being present in the heart of the patient based on whether the intrinsic delay is less than a threshold; and based on the intrinsic delay not being indicative of the first-degree heart block being present in the heart of the patient, determines the patient-specific timing regime based on a minimum of: (i) a coefficient multiplied by the intrinsic delay, and (ii) a difference between the intrinsic delay and the pace-activation delay.

Example 21: The system of any of examples 18-19, wherein the processing circuitry is configured such that, as part of determining the patient-specific timing regime, the processing circuitry: determines whether the intrinsic delay is indicative of the first-degree heart block being present in the heart of the patient based on whether the intrinsic delay is greater than a threshold; and based on the intrinsic delay being indicative of the first-degree heart block being present in the heart of the patient, determines the patient-specific timing regime based on a minimum of: (i) a sum of a delay between an atrial sense event or an atrial pacing event and an end of a P-wave of the heart and a programmable value minus the pace-activation delay, and (ii) a difference between the intrinsic delay and the pace-activation delay.

Example 22: The system of any of examples 13-21, wherein: the processing circuitry is further configured to: determine a baseline QRS delay based on the signals, wherein the baseline QRS delay is based on a set of determined differences in time between an atrial sense event or an atrial pace event to an end of a QRS complex; determine a current QRS delay based on the signals, wherein the current QRS delay is a difference in time between a current atrial sense event or a current atrial pace event and an end of a current QRS complex; determine, whether a difference between the current QRS delay and the baseline QRS delay is greater than a threshold; and based on the difference between the current QRS delay and the baseline QRS delay being greater than the threshold, adjust the patient-specific timing regime, and the therapy delivery circuitry is configured to administer the cardiac pacing to the native conduction system of the heart of the patient based on the adjusted timing regime.

Example 23: The system of any of examples 13-22, wherein: the processing circuitry is configured such that, as part of adjusting the patient-specific timing regime, the processing circuitry: determines, based on the signals, a second intrinsic delay of the heart of the patient; determines whether the second intrinsic delay is indicative of the first-degree heart block being present in the heart of the patient; determines a second patient-specific timing regime for conduction system pacing based on the second intrinsic delay and whether the second intrinsic delay is indicative of the first-degree heart block being present in the heart of the patient; and the therapy delivery circuitry is configured to administer the cardiac pacing to the native conduction system of the heart of the patient based on the second patient-specific timing regime.

Example 24: The system of any of examples 13-23, wherein the processing circuitry is configured to determine the patient-specific timing regime for conduction system pacing based on the intrinsic delay and whether the intrinsic delay is indicative of the first-degree heart block being present in the heart of the patient.

Example 25: A non-transitory computer-readable medium storing instructions for causing processing circuitry of an implantable medical device system to perform a method of any of examples 1-12.

Various aspects of the techniques may be implemented within one or more processing circuitries, including one or more microprocessors, DSPs, ASICs, FPGAs, or any other equivalent integrated or discrete logic circuitry, as well as any combinations of such components, embodied in external devices, such as physician or patient external devices, electrical stimulators, or other devices. The term "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processing circuitries, such as one or more DSPs, ASICs, FPGAs, general purpose microprocessors, or other equivalent integrated or discrete logic circuitry. Accordingly, the term "processing circuitry," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external device, a combination of an IMD and external device, an integrated circuit (IC) or a set of ICs, and/or discrete electrical circuitry, residing in an IMD and/or external device.

The invention claimed is:

1. A method comprising:
generating, by sensing circuitry of an implantable medical device system, signals representing activity of a heart of a patient;
determining, by processing circuitry of the implantable medical device system, based on the signals, an intrinsic delay of the heart of the patient;
determining, by the processing circuitry, whether the intrinsic delay is indicative of a first-degree heart block being present in the heart of the patient;
determining, by the processing circuitry, a patient-specific timing regime for conduction system pacing based on whether the intrinsic delay is indicative of the first-degree heart block being present in the heart of the patient;
administering, by therapy delivery circuitry of the implantable medical device system, cardiac pacing to a native conduction system of the heart of the patient based on the patient-specific timing regime;
determining, by the processing circuitry, a baseline QRS delay based on the signals, wherein the baseline QRS delay is based on a set of determined differences in time between an atrial sense event or an atrial pace event to an end of a QRS complex;
determining, by the processing circuitry, a current QRS delay based on the signals, wherein the current QRS delay is a difference in time between a current atrial sense event or a current atrial pace event and an end of a current QRS complex;

determining, by the processing circuitry, whether a difference between the current QRS delay and the baseline QRS delay is greater than a threshold; and based on the difference between the current QRS delay and the baseline QRS delay being greater than the threshold:
  adjusting, by the processing circuitry, the patient-specific timing regime; and
  administering, by the therapy delivery circuitry, the cardiac pacing to the native conduction system of the heart of the patient based on the adjusted timing regime.

2. The method of claim 1, wherein:
administering the cardiac pacing comprises administering ventricular pacing,
generating the signals comprises generating, by the sensing circuitry, signals representing activity of the heart of the patient while ventricular pacing is paused;
determining the intrinsic delay comprises determining, by the processing circuitry, based on the signals representing activity of the heart of the patient while ventricular pacing is paused, the intrinsic delay as one of:
  a time between sensing of a depolarization of a right atrium of the heart of the patient and an activation of a right ventricle of the heart of the patient, or
  a time between an atrial pace event of the right atrium of the heart of the patient and the activation of the right ventricle of the heart of the patient.

3. The method of claim 1, wherein generating signals representing activity of the heart of the patient comprises generating a far-field electrogram, the method further comprising determining, by the processing circuitry, the activation of the right ventricle of the heart of the patient using the far-field electrogram.

4. The method of claim 1, wherein the cardiac pacing comprises left bundle branch pacing and the method further comprises:
  determining, by the processing circuitry, whether left bundle branch block is present; and
  based on left bundle branch block not being present in the heart of the patient, suspending, by the therapy delivery circuitry, the left bundle branch pacing.

5. The method of claim 1, wherein determining whether the first-degree heart block is present comprises determining, by the processing circuitry, whether the intrinsic delay is greater than an intrinsic delay threshold.

6. The method of claim 1, wherein:
the method further comprises:
  administering, by the therapy delivery circuitry, a pacing pulse to the native conduction system of the heart of the patient; and
  determining, by the processing circuitry, a pace-activation delay based on the signals, wherein the pace-activation delay indicates a time between delivery of the pacing pulse and an earliest onset of ventricular activation, and
determining the patient-specific timing regime comprises determining, by the processing circuitry, the patient-specific timing regime based on the intrinsic delay, whether the intrinsic delay is indicative of the first-degree heart block being present in the heart of the patient, and the pace-activation delay.

7. The method of claim 6, wherein the pacing pulse is a premature pacing pulse.

8. The method of claim 1, wherein adjusting the patient-specific timing regime comprises:
  determining, by the processing circuitry, based on the signals, a second intrinsic delay of the heart of the patient;
  determining, by the processing circuitry, whether the second intrinsic delay is indicative of the first-degree heart block being present in the heart of the patient;
  determining, by the processing circuitry, a second patient-specific timing regime for conduction system pacing based on the second intrinsic delay and whether the second intrinsic delay is indicative of the first-degree heart block being present in the heart of the patient; and
  administering, by the therapy delivery circuitry, the cardiac pacing to the native conduction system of the heart of the patient based on the second patient-specific timing regime.

9. The method of claim 1, wherein determining the patient-specific timing regime for conduction system pacing comprises determining the patient-specific timing regime for conduction system pacing based on the intrinsic delay and whether the intrinsic delay is indicative of the first-degree heart block being present in the heart of the patient.

10. A method comprising:
  generating, by sensing circuitry of an implantable medical device system, signals representing activity of a heart of a patient;
  determining, by processing circuitry of the implantable medical device system, based on the signals, an intrinsic delay of the heart of the patient;
  determining, by the processing circuitry, whether the intrinsic delay is indicative of a first-degree heart block being present in the heart of the patient based on whether the intrinsic delay is less than a threshold;
  administering, by therapy delivery circuitry of the implantable medical device system, a pacing pulse to the native conduction system of the heart of the patient;
  determining, by the processing circuitry, a pace-activation delay based on the signals, wherein the pace-activation delay indicates a time between delivery of the pacing pulse and an earliest onset of ventricular activation;
  determining, by the processing circuitry, a patient-specific timing regime for conduction system pacing based on the intrinsic delay, whether the intrinsic delay is indicative of the first-degree heart block being present in the heart of the patient, and the pace-activation delay, wherein to determine the patient-specific timing regime, the processing circuitry is configured to, based on the intrinsic delay not being indicative of the first-degree heart block being present in the heart of the patient, determining, by the processing circuitry, the patient-specific timing regime based on a minimum of: (i) a coefficient multiplied by the intrinsic delay, and (ii) a difference between the intrinsic delay and the pace-activation delay; and
  administering, by the therapy delivery circuitry, cardiac pacing to a native conduction system of the heart of the patient based on the patient-specific timing regime.

11. A method comprising:
  generating, by sensing circuitry of an implantable medical device system, signals representing activity of a heart of a patient;
  determining, by processing circuitry of the implantable medical device system, based on the signals, an intrinsic delay of the heart of the patient;
  determining, by the processing circuitry, whether the intrinsic delay is indicative of a first-degree heart block being present in the heart of the patient based on whether the intrinsic delay is greater than a threshold;

administering, by the therapy delivery circuitry, a pacing pulse to the native conduction system of the heart of the patient; and determining, by the processing circuitry, a pace-activation delay based on the signals, wherein the pace-activation delay indicates a time between delivery of the pacing pulse and an earliest onset of ventricular activation;

determining, by the processing circuitry, a patient-specific timing regime for conduction system pacing based on the intrinsic delay, whether the intrinsic delay is indicative of the first-degree heart block being present in the heart of the patient, and the pace-activation delay, wherein to determine the patient-specific timing regime, the processing circuitry is configured to, based on the intrinsic delay being indicative of the first-degree heart block being present in the heart of the patient, determining, by the processing circuitry, the patient-specific timing regime based on a minimum of: (i) a sum of a delay between an atrial sense event or an atrial pacing event and an end of a P-wave of the heart and a programmable value minus the pace-activation delay, and (ii) a difference between the intrinsic delay and the pace-activation delay; and administering, by the therapy delivery circuitry, cardiac pacing to a native conduction system of the heart of the patient based on the patient-specific timing regime.

12. An implantable medical device system comprising:
sensing circuitry configured to generate signals representing activity of a heart of a patient;
processing circuitry configured to:
   determine, based on the signals, an intrinsic delay of the heart of the patient;
   determine whether the intrinsic delay is indicative of a first-degree heart block being present in the heart of the patient;
   determine a patient-specific timing regime for conduction system pacing based on whether the intrinsic delay is indicative of the first-degree heart block being present in the heart of the patient; control therapy delivery circuitry to administer cardiac pacing to a native conduction system of the heart of the patient based on the patient-specific timing regime;
   determine a baseline QRS delay based on the signals, wherein the baseline QRS delay is based on a set of determined differences in time between an atrial sense event or an atrial pace event to an end of a QRS complex;
   determine a current QRS delay based on the signals, wherein the current QRS delay is a difference in time between a current atrial sense event or a current atrial pace event and an end of a current QRS complex;
   determine, whether a difference between the current QRS delay and the baseline QRS delay is greater than a threshold; and
   based on the difference between the current QRS delay and the baseline QRS delay being greater than the threshold, adjust the patient-specific timing regime; and
the therapy delivery circuitry configured to administer the cardiac pacing to the native conduction system of the heart of the patient based on the adjusted patient-specific timing regime.

13. The system of claim 12, wherein:
the cardiac pacing comprises ventricular pacing,
the sensing circuitry is configured such that, as part of generating the signals, the sensing circuitry generate signals representing activity of the heart of the patient while ventricular pacing is paused;
the processing circuitry is configured such that, as part of determining the intrinsic delay, the processing circuitry determines, based on the signals representing activity of the heart of the patient while ventricular pacing is paused, the intrinsic delay as one of:
   a time between sensing of a depolarization of a right atrium of the heart of the patient and an activation of a right ventricle of the heart of the patient, or
   a time between an atrial pace event of the right atrium of the heart of the patient and the activation of the right ventricle of the heart of the patient.

14. The system of claim 12, wherein signals representing activity of the heart of the patient comprise a far-field electrogram, wherein the processing circuitry is further configured to determine the activation of the right ventricle of the heart of the patient using the far-field electrogram.

15. The system of claim 12, wherein the cardiac pacing comprises left bundle branch pacing and the system is further configured to determine whether left bundle branch block is present, and the therapy delivery circuitry is configured to suspend, based on left bundle branch block not being present in the heart of the patient, the left bundle branch pacing.

16. The system of claim 12, wherein the processing circuitry is configured such that, as part of determining whether the first-degree heart block is present, the processing circuitry determines whether the intrinsic delay is greater than an intrinsic delay threshold.

17. The system of claim 12, wherein:
the therapy delivery circuitry is further configured to administer a pacing pulse to the native conduction system of the heart of the patient,
the processing circuitry is configured to determine a pace-activation delay based on the signals, wherein the pace-activation delay indicates a time between delivery of the pacing pulse and an earliest onset of ventricular activation, and
the processing circuitry is configured such that, as part of determining the patient-specific timing regime, the processing circuitry determines the patient-specific timing regime based on the intrinsic delay, whether the intrinsic delay is indicative of the first-degree heart block being present in the heart of the patient, and the pace-activation delay.

18. The system of claim 17, wherein the pacing pulse is a premature pacing pulse.

19. The system of claim 12, wherein:
the processing circuitry is configured such that, as part of adjusting the patient-specific timing regime, the processing circuitry:
   determines, based on the signals, a second intrinsic delay of the heart of the patient;
   determines whether the second intrinsic delay is indicative of the first-degree heart block being present in the heart of the patient;
   determines a second patient-specific timing regime for conduction system pacing based on the second intrinsic delay and whether the second intrinsic delay is indicative of the first-degree heart block being present in the heart of the patient; and
the therapy delivery circuitry is configured to administer the cardiac pacing to the native conduction system of the heart of the patient based on the second patient-specific timing regime.

20. The system of claim 12, wherein the processing circuitry is configured to determine the patient-specific timing regime for conduction system pacing based on the intrinsic delay and whether the intrinsic delay is indicative of the first-degree heart block being present in the heart of the patient.

21. An implantable medical device system comprising:
sensing circuitry configured to generate signals representing activity of a heart of a patient;
therapy delivery circuitry configured to administer cardiac pacing to a native conduction system of the heart;
processing circuitry configured to:
determine, based on the signals, an intrinsic delay of the heart of the patient;
determine whether the intrinsic delay is indicative of a first-degree heart block being present in the heart of the patient based on whether the intrinsic delay is less than a threshold;
control the therapy delivery circuitry to administer a cardiac pacing pulse to a native conduction system of the heart of the patient;
determine a pace-activation delay based on the signals, wherein the pace-activation delay indicates a time between delivery of the pacing pulse and an earliest onset of ventricular activation;
determine a patient-specific timing regime for conduction system pacing based on the intrinsic delay, whether the intrinsic delay is indicative of the first-degree heart block being present in the heart of the patient, and the pace-activation delay;
based on the intrinsic delay being indicative of the first-degree heart block being present in the heart of the patient, determine the patient-specific timing regime based on a minimum of: (i) a coefficient multiplied by the intrinsic delay, and (ii) a difference between the intrinsic delay and the pace-activation delay; and
control the therapy delivery circuitry to administer cardiac pacing to the native conduction system of the heart of the patient based on the patient-specific timing regime.

22. An implantable medical device system comprising:
sensing circuitry configured to generate signals representing activity of a heart of a patient;
therapy delivery circuitry configured to administer cardiac pacing to a native conduction system of the heart;
processing circuitry configured to:
determine, based on the signals, an intrinsic delay of the heart of the patient;
determine whether the intrinsic delay is indicative of the first-degree heart block being present in the heart of the patient based on whether the intrinsic delay is greater than a threshold;
control the therapy delivery circuitry to administer a pacing pulse to the native conduction system of the heart;
determine a pace-activation delay based on the signals, wherein the pace-activation delay indicates a time between delivery of the pacing pulse and an earliest onset of ventricular activation;
determine a patient-specific timing regime for conduction system pacing based on the intrinsic delay, whether the intrinsic delay is indicative of the first-degree heart block being present in the heart of the patient, and the pace-activation delay;
based on the intrinsic delay being indicative of the first-degree heart block being present in the heart of the patient, determine the patient-specific timing regime based on a minimum of: (i) a sum of a delay between an atrial sense event or an atrial pacing event and an end of a P-wave of the heart and a programmable value minus the pace-activation delay, and (ii) a difference between the intrinsic delay and the pace-activation delay; and
control the therapy delivery circuitry to administer cardiac pacing to the native conduction system of the heart based on the patient-specific timing regime.

23. A non-transitory computer-readable medium storing instructions for causing processing circuitry of an implantable medical device system to:
generate signals representing activity of a heart of a patient;
determine, based on the signals, an intrinsic delay of the heart of the patient;
determine whether the intrinsic delay is indicative of a first-degree heart block being present in the heart of the patient;
determine a patient-specific timing regime for conduction system pacing based on whether the intrinsic delay is indicative of the first-degree heart block being present in the heart of the patient;
control administration of cardiac pacing to a native conduction system of the heart of the patient based on the patient-specific timing regime;
determine a baseline QRS delay based on the signals, wherein the baseline QRS delay is based on a set of determined differences in time between an atrial sense event or an atrial pace event to an end of a QRS complex;
determine a current QRS delay based on the signals, wherein the current QRS delay is a difference in time between a current atrial sense event or a current atrial pace event and an end of a current QRS complex;
determine whether the difference between the current QRS delay and the baseline QRS delay is greater than a threshold;
based on the difference between the current QRS delay and the baseline QRS delay being greater than the threshold, adjust the patient-specific timing regime; and
control administration of the cardiac pacing to a native conduction system of the heart of the patient based on the adjusted patient-specific timing regime.

* * * * *